United States Patent [19]

Nishino et al.

[11] Patent Number: 6,075,045
[45] Date of Patent: Jun. 13, 2000

[54] METHOD OF TREATING PARALYSIS OF THE EXTREMITIES CAUSED BY CEREBRAL INFARCTION

[75] Inventors: Hitoo Nishino, Nagoya, Japan; Cesario V. Borlongan, Silver Spring, Md.; Hisayuki Uneyama, Kawasaki, Japan

[73] Assignee: Ajinomoto Co., Inc., Tokyo, Japan

[21] Appl. No.: 09/300,456

[22] Filed: Apr. 28, 1999

[51] Int. Cl.$^7$ .............................................. A61K 31/4045
[52] U.S. Cl. ............................................................ 514/419
[58] Field of Search .............................................. 514/419

[56] References Cited

FOREIGN PATENT DOCUMENTS

WO 97/20555   6/1997   WIPO .

OTHER PUBLICATIONS

Maestroni et al., Immunology, 63(3), 465–470 (abstract), 1988.
Chemical & Engineering News, p. 40, "The Biochemically Active Pineal Gland May Be As Important As Any Other", May 1, 1967.
J. Barchas, et al., Nature, vol. 214, pp. 919–920, "Acute Pharmacology of Melatonin", May 27, 1967.
A. Miles, et al., CRC Critical Reviews in Clinical Laboratory Sciences, vol. 25, Issue 3, pp. 231–253, "Melatonin: Perspectives In Laboratory Medicine and Clinical Research", 1987.
R. Reiter, et al., Life Sciences, vol. 60, No. 25, pp. 2255–2271, "Pharmacological Actions Of Melatonin In Oxygen Radical Pathophysiology", 1997.
J.M. Guerrero, et al., J. Pineal Res., vol. 23, pp. 24–31, Melatonin Prevents Increases In Neural Nitric Oxide and Cyclic GMP Production After Transient Brain Ischemia And Reperfusion In The Mongolian Gerbil (Meriones Unguiculatus), 1997.
S. Cho, et al., Brain Research, vol. 755, pp. 335–338, "Melatonin Administration Protects CA1 Hippocampal Neurons After Transient Forebrain Ischemia In Rats", 1997.
M.D. Ginsberg, et al., Stroke, vol. 20, No. 12, pp. 1627–1642, "Rodent Models Of Cerebral Ischemia", Dec., 1989.
H. Manev, et al., The FASEB Journal., vol. 10, pp. 1546–1551, "Increased Brain Damage After Stroke Or Excitotoxic Seizures In Melatonin–Deficient Rats", Nov., 1996.
R.J. Reiter, Acta Neurobiologiæ Experimentalis, vol. 54 (Suppl.), pp. 31–39, "Pineal Function During Aging: Attenuation Of The Melatonin Rhythm and Its Neurobiological Consequences", 1994.
R.J. Reiter, The FASEB Journal., vol. 9, No. 7, pp. 526–533, "Oxidative Processes And Antioxidative Defense Mechanisms In The Aging Brain", May, 1995.
E.A. Lane, et al., The Journal of Clinical Endocrinology and Metabolism, vol. 61, No. 6, pp. 1214–1216, "Pharmacokinetics Of Melatonin In Man: First Pass Hepatic Metabolism", Dec., 1985.
O. Vakkuri, et al., Life Sciences, vol. 37, pp. 489–495, "Oral Administration And Distribution Of Melatonin In Human Serum, Saliva And Urine", 1985.
M. Aldhous, et al., British Journal of Clinical Pharmacology, vol. 19, No. 4, pp. 517–521, "Plasma Concentrations Of Melatonin In Man Following Oral Absorption Of Different Preparations", Apr., 1985.
F. Waldhauser, et al., Neuroendocrinology, vol. 39, No. 4, pp. 307–313, "Bioavailability Of Oral Melatonin In Humans", Oct., 1984.
P.A. Vitte, et al., Journal of Pineal Research, vol. 5, No. 5, pp. 437–453, "Plasma, Cerebrospinal Fluid, And Brain Distribution Of $^{14}$C–Melatonin In Rat: A Biochemical And Autoradiographic Study", 1988.
D. Le Bars, et al., International Journal of Radiation Applications and Instrumentation Part B, vol. 18, No. 3, pp. 357–362, "Pet And Plasma Pharmacokinetic Studies After Bolus Intravenous Administration Of [$^{11}$C]Melatonin In Humans", 1991.
W.A. Pulsinelli, et al., Stroke, vol. 10, pp. 267–272, "A New Model Of Bilateral Hemispheric Ischemia In The Unanesthetized Rat", 1979.

*Primary Examiner*—Phyllis G. Spivack
*Attorney, Agent, or Firm*—Oblon, Spivak, McClelland, Maier & Neustadt, P.C.

[57] ABSTRACT

The administration of a therapeutically effective amount of melatonin is an effective method for treating paralysis of the extremities caused by cerebral infarction.

8 Claims, No Drawings

METHOD OF TREATING PARALYSIS OF THE EXTREMITIES CAUSED BY CEREBRAL INFARCTION

BACKGROUND OF THE INVENTION

1. Field of the Invention

The present invention relates to a method for the treatment of paralysis of the extremities induced by cerebral infarction. More specifically, it relates to a method comprising administering melatonin for the treatment of such paralysis of the extremities.

2. Discussion of the Background

Cerebral infarction is a severe cerebral dysfunction induced by cerebral ischemia or hypoxemia. With the increase of the aged population, the incidence of diseases or conditions, which may cause cerebral ischemia such as cerebral thrombosis and cerebral embolism, is increasing. Indeed, the number of patients suffering from cerebral infarction and having cerebral dysfunctions is continuously increasing.

One of the cerebral dysfunctions caused by cerebral infarction is paralysis of the extremities. When the hands and legs cannot perform their functions, the quality of life of such affected patients is significantly lowered and many burdens are placed on them and their families. For such patients, complete daily care is necessary.

For the treatment of severe cerebral infarction resulting in paralysis of the extremities, the use of a neuroprotective (e.g., as a glutamic acid antagonist, a channel antagonist, a radical scavenger, a neurogrowth factor, and a GABA agonist) has been proposed, but it requires further basic study. A central muscle relaxant, an agent for improving the microcirculation (e.g., an anti-platelet drug and an agent for accelerating deformation of erythrocytes), an agent for improving cerebral metabolism (e.g., an agent for enhancing the GABA system or the dopamine system and an agent for regulating the acetylcholine system), and the like have been complementarily administered in order to reduce adverse influences of cerebral infarction. Further, physiotherapies, such as a motorpathy, have been conducted in order to treat motor dysfunctions of the extremities caused by cerebral infarction.

Melatonin (N-[2-(5-methoxy-1H-indol-3-yl)ethyl] acetamide) is secreted from the pineal gland, and acts upon the suprachiasmatic nucleus to influence the formation of a diurnal rhythm (e.g., Chem. & Eng. News, vol. 45, p. 40 (1967)).

Since melatonin is characterized by the above physiological action, it is used for the treatment of disorders of the diurnal rhythm, such as sleep disorders, emotional disorders, immune hypofunctions, caused by, for example, time-difference (jetlag) (e.g., Barchas et al., Nature, vol. 214, p. 919 (1967) and A. Miles, D. Philbrick, CRC Crit. Rev. Clin. Lab. Sci., vol. 25, pp. 231–253 (1987)).

It was also reported that melatonin has antioxidative activity and functions as a free radical scavenger in vivo (Life Sci., vol. 60(25), pp. 2255–2271 (1997)).

The possibility that administered melatonin inhibits brain nitric oxide (NO) production after transient cerebral ischemia/reperfusion and reduces brain damage caused by free radicals has been mentioned (Guerrero J M. et al., J. Pineal Res., 23(1), 24–3 1(1997)).

Further, Sunghee Cho et al. (Brain Res., vol. 755(2), pp.335–338 (1997)) described that intraperitoneally administered melatonin, especially prior to cerebral ischemia or during reperfusion, protects CA1 hippocampal neurons against ischemic injury. However, it has been known that severe cerebral dysfunctions, which may result in paralysis of the extremities, do not occur in cases where the injury caused by cerebral ischemia is restricted to the hippocampus. Also, no extra-hippocampal damage was observed (Ginsburg et al., Rodent models of Cerebral Ischemia, Stroke, vol. 20, pp. 1627–1642 (1989)).

In addition, it has been reported that in models of cerebral ischemia induced by ligating the middle cerebral artery, the brain necroses (by observation of tissues under a microscope) of rats having no detectable level of blood melatonin after pinealectomy are significantly greater than in normal rats (Manev H. et al., FASEB J, vol. 10(13), pp. 1546–1551 (1996)). However, this report does not suggest the role of exogenous melatonin in the presence of endogenous melatonin, since cerebral ischemia was not induced in the presence of endogenous melatonin.

It has been reported that blood (endogenous) melatonin in old men of the age of 82 to 86 is about one quarter of that in young men of the age of 21 to 25 (about 80 pg/ml) (Reiter R. J., Acta Neurobiol. Exp., vol. 54, pp. 31–39 (1994) and Reiter R. J., FASEB J., vol. 9, pp. 526–533 (1995)).

On the other hand, it is described in J. Clin. Endocrinol. Metab., vol. 61, pp. 1214–1216 (1985); Life Sci., vol. 37, pp. 489–495 (1985); Br. J. Clin. Pharmacol., vol. 19, pp. 517–521 (1985); and Neuroendocrinology, vol. 39, pp. 307–313 (1984) that orally administered melatonin circulates in the blood and passes through the blood-brain barrier. Also, intravenously administered melatonin was shown to pass into the brain (Pineal Res., vol. 5, pp. 437–453 (1988) and Int. J. Rds. Appl. Instrum. [B], vol. 18, pp. 357–362 (1991)).

WO 97/20555 (corresponding to U.S. Pat. No. 5,700,828) discloses that the mild motor dysfunction of a foot-fault rate of 0.01 in rats caused by cerebral ischemia can be lowered to a foot-fault rate of 0.002 by administration of a "rescue" solution containing melatonin, kynurenine and others to the cerebral ischemic rat. The foot fault rate of the non-treated control rats was 0.005 in the experiment.

However, in the transient ischemic rat model employed in WO 97/20555, wherein the bilateral vertebral arteries were ligated (in practice, burned off) and one day later the bilateral internal carotid arteriae were occluded for 10 minutes (Stroke, vol. 10, pp. 267–272 (1979)), the rats would suffer from neuropathies (e.g., extremital peripheral nerve disturbances, muscle disturbances, equilibrium disturbances, and visual disturbances) resulting from causes other than cerebral infarction. Ataxia would be caused by the neuropathies, leading to the lowering in foot-fault rate. In fact, no cerebral infarction could be demonstrated with other experiments in transient ischemic rats produced by the procedures as above. Further, the motor dysfunction of a foot-fault rate of 0.01 in the transient ischemic rats of WO 97/20555 is not so severe as to cause paralysis of extremities.

The foot fault rate is a known term, and is generally determined according to the Hernandez-Schallert foot-fault test, wherein rats are forced to walk on a bar 3 to 6 cm in diameter, and the percentage of missed steps (slipped down) is calculated. The rate is the proportion of the missed steps after ischemia to the missed steps before ischemia.

Accordingly, WO 97/20555 fails to suggest the treatment of severe cerebral infarction which may causes paralysis of the extremities, or severe paralysis of the extremities resulting from cerebral infarction.

Thus, there remains a need for an effective method capable of treating paralysis of the extremities caused by cerebral infarction.

SUMMARY OF THE INVENTION

Accordingly, it is one object of the present invention to provide a method capable of treating paralysis of the extremities caused by cerebral infarction.

After exhaustive research, the present inventors have found that melatonin acts to treat paralysis of the extremities caused by cerebral infarction.

Therefore, the present invention provide a method capable of treating paralysis of the extremities caused by cerebral infarction comprising administering a therapeutically effective amount of melatonin to a subject suffering from paralysis of the extremities caused by cerebral infarction.

DETAILED DESCRIPTION OF THE PREFERRED EMBODIMENTS

Thus, the present invention provides a method of treating paralysis of the extremities caused by cerebral infarction comprising administering a therapeutically effective amount of melatonin to a subject suffering from paralysis of the extremities caused by cerebral infarction. The term "paralysis of extremities" as used herein means that at least one of the hands or feet is paralytic. The term "paralysis" as used herein represents the condition where the extremities cannot be voluntarily moved, i.e., a patient suffering from paralysis of the hands as used herein is incapable of catching or lifting up a light article and of bringing food to the mouth, and a patient suffering from "paralysis" of the legs as used herein cannot stand even if a fixed appliance such as a handrail is used.

Therefore, the term "paralysis" as used herein is distinct from a motor disturbance where a patient suffering from paralysis of the hands can catch or lift up a light article and a patient suffering from paralysis of the legs can stand at least by using a fixed appliance, or from disturbances at a lesser extent.

The term "cerebral infarction" as used herein means an infarction in any tissue or part of the brain including lacunae infarctions. Cerebral infarction is induced by cerebral ischemia or hypoxemia. As is well known, major causes of cerebral ischemia are cerebral thrombosis and cerebral embolism. Cerebral infarction itself may be the cause of an additional cerebral ischemia. Cerebral infarction resulting from the condition of cerebral thrombosis may be referred to as "cerebral thrombosis." Also, cerebral infarction resulting from the condition of cerebral embolism may be referred to as "cerebral embolism." The term "cerebral infarction" as used herein includes such cerebral thrombosis and cerebral embolism of the usage as above.

Melatonin may be advantageously administered in a form in which it is encapsulated in an encapsulating matrix, liposomes or the like. Melatonin encapsulated in an encapsulating matrix or liposomes is gradually released into the blood so that its apparent residence time in the blood is increased, leading to an increase in the availability of melatonin.

Examples of suitable encapsulating matrices are cyclodextrin and pharmaceutically acceptable biodegradable synthetic or natural polymers such as polylactic acid, a copolymer of lactic acid with glycol, and poly-β-hydroxybutyric acid. A plurality of cyclodextrins attached onto a pharmaceutically acceptable synthetic polymer is included in the definition of cyclodextrin.

Suitable methods for preparing liposomes include the various known methods such as the vortex method (Bangham AD et al., Methods Membr. Biol., vol. 1, p. 1–22 (1974)); the ultrasonic treatment method (Johnson SM et al., Biochem. Biophys. Acta, vol. 233, p. 820–826 (1971)); the ethanol injection method (Kremer J M H et al., Biochemistry, vol. 16, pp. 3932–3941(1980)); the French-Press method (Hamilton et al., J. Lipid Res., vol. 21, pp. 981–982 (1980)); the cholic acid removal method (Enoch HG et al., Proc. Natl. Acad. Sci., vol. 76, pp. 145–149 (1979)); the ether injection method (Deamer DN, Ann. N.Y. Acad. Sci., vol. 308, pp. 250–258 (1987)); the freeze-thaw method (Papahadjopoulos D et al., Biochim. Biophys. Acta, vol. 394, pp. 483–491 (1975)); and the reverse phase evaporation method (Szoka F et al., Proc. Natl. Acad. Sci. USA, vol. 75, pp. 4191–4198 (1978)); the disclosures, with respect to the methods for the preparation of liposomes, of all of which are incorporated herein by reference.

The amount of melatonin to be administered to a patient having paralysis of the extremities caused by cerebral infarction depends on various factors including sex, age, body weight and diet of the patient; the administration route; the condition and/or degree of cerebral thrombosis and cerebral embolism; the condition and/or degree of cerebral infarction; and the like. It is fully dependent on a clinician.

The daily dose of the pharmaceutical composition of the present invention is generally determined in such a manner that the melatonin blood concentration per day ranges from 10 ng/ml to 300 μg/ml, preferably from 50 μg/ml to 100 μg/ml. The term "blood concentration per day" means the total blood concentration of melatonin administered in a day. For example, in the case when a first administration gives a blood concentration of 50 μg/ml and a second administration given on the same day as the first administration gives a concentration of 30 μg/ml, the blood concentration per day is 80 μg/ml.

Since the availability of melatonin varies depending on various factors (e.g., administration route, dosage form, encapsulation of melatonin, and age of the patient), the daily dose of the pharmaceutical composition is naturally adjusted to maintain the above blood concentration.

In the case of oral administration, melatonin should be administered to the patient in an amount of about 0.8 mg/kg per day to attain a melatonin blood concentration of 100 ng/ml.

When the melatonin is encapsulated in an encapsulating matrix or a liposome, its amount is expressed in terms of free (non-encapsulated) melatonin. Since melatonin in an encapsulated form is gradually released into the blood, its apparent residence time in the blood is longer. Thus, the melatonin blood concentration in the encapsulated form of melatonin may be lower than the above blood concentrations of melatonin in the free form.

The melatonin can be administered by various routes, such as permucosally (e.g., sublingually, intranasally, oral mucosally), orally, enterally, percutaneously, intravenously, by aspiration, by suppository, or by instillation. The administration route is determined by a clinician depending on the amount of melatonin to be administered, and the condition of the patient.

Generally, patients having paralysis of the extremities caused by cerebral infarction require treatment for a long period and desire to stay home, while undergoing treatment. Oral administration of the pharmaceutical composition to such patients is preferable.

The melatonin is typically administered in the form of a pharmaceutical composition which comprises melatonin and a pharmaceutical carrier. The term "pharmaceutical carrier" as used herein includes any ingredient which is pharmaceutically acceptable and physiologically lessactive.

The melatonin may be administered as a single or multiple daily doses or may be administered via a controlled-release or sustained-release formulation. The composition for oral administration is preferably in the form of a sustained-release formulation. For the sustained release, conventional sustained or controlled release formulations (e.g., a formulation having a gel coating and a formulation having multiple coatings) and formulations for local release (e.g., a formulation capable of rupturing in the pylorus or a formulation capable of foaming in the duodenum) are well known and may be used.

Examples of the composition for oral administration include tablets, pills, capsules, ampuls, folded powders, elixirs, suspensions, syrups and the like.

When the pharmaceutical composition is orally administered, binders such as tragacanth gum, acacia, corn starch and gelatin; vehicles such as potassium diphosphate; disintegrators such as potato starch and alginic acid; lubricants such as magnesium stearate; sweetening agents such as sucrose; dyes; perfumes such as orange flavor; solvents such as water, ethanol, and glycerol can be suitably used as the pharmaceutical carrier.

When a pharmaceutically acceptable antioxidant such as cysteine, glutathione, ascorbic acid, sodium metasulfite, or sodium bisulfite is added to the pharmaceutical composition of the present invention to be orally administered, favorable results may be obtained.

Also, nutrients such as amino acids, vitamins, lipids and glucose are suitably added to the pharmaceutical composition of the present invention to be orally administered.

The pharmaceutical composition for injection of the present invention may contain, for example, sterile water, an isotonic saline solution, or a pH butter as a pharmaceutical carrier, or may be a sterile powder composition, a freeze-dried powder composition or the like, which can be used merely by dissolving in a sterile water or other suitable solvent.

The pharmaceutical composition for injection of the present invention may contain saccharides such as glucose, mannitol, and dextran; polyhydric alcohols such as glycerol; inorganic salts such as sodium salt and magnesium salt. Further, it may contain a pharmaceutically acceptable antioxidant such as cysteine, glutathione, ascorbic acid, sodium metasulfite, or sodium bisulfite.

When the pharmaceutical composition of the present invention is administered by instillation, it may contain nutrients such as glucose, vitamins, amino acids, and lipids.

Pharmaceutical carriers contained in dosage forms for other administration routes such as intranasal, aspiration or percutaneous administrations are well known.

The dosage forms and the pharmaceutical carriers mentioned above are described in Reimington's Pharmaceutical Science, ed. 16 (1980), Mack Publishing company, which is incorporated herein by reference.

Further, the pharmaceutical composition of the present invention may contain any therapeutic agents for the treatment of the diseases or conditions which may induce cerebral ischemia such as cerebral thrombosis and cerebral embolism, together with melatonin.

Known therapeutic agents for cerebral embolism include anti-edema drugs, anticoagulants, thrombolytic drugs, and calcium antagonists. Known therapeutic agents for cerebral thrombosis include anti-edema drugs, anti-platelet drugs, and calcium antagonists.

Also, the pharmaceutical composition of the present invention may contain a therapeutic agent used for reducing adverse influences of cerebral infarction such as a central muscle relaxant, an agent for accelerating microcirculation, and an agent for improving cerebral metabolism.

In some cases, the pharmaceutical composition of the present invention may contain an auxiliary amount of a neuroprotective, which may cooperatively function with melatonin in the treatment of paralysis of the extremities resulting from cerebral infarction.

The above therapeutic agents or neuroprotectives may be added to a pharmaceutical composition for oral administration of the present invention if they can be orally administered. Alternatively, they may be added to a pharmaceutical composition for parenteral administration including injection if they cannot be orally administered. The amount of each therapeutic agent or neuroprotective in the pharmaceutical composition for oral or parenteral administration can be also determined by a clinician.

It is preferred to commence treatment with melatonin as quickly as possible and as soon after the cerebral infarction as possible. However, it is possible to commence treatment after the diagnosis of paralysis of the extremities, and administration of melatonin is effective even after a prolonged delay of one, two, three, or more days after the ischemia-reperfusion event. The melatonin therapy is typically continued until the desired level of improvement is observed in the patient.

Other features of the invention will become apparent in the course of the following descriptions of exemplary embodiments which are given for illustration of the invention and are not intended to be limiting thereof.

EXAMPLES

EXAMPLE 1.

Eight to ten-week-old male Wister rats weighing of 250 to 300 g were used.

Under halothane anesthesia, a 24 G (24 gauge) plug was inserted from a right external carotid artery of each rat so as to arrive to a starting site of its middle cerebral artery of the circle of Willis through its internal carotid artery. Immediately, the anesthesia was stopped, and the rat was dehypnotized. It was confirmed that the rat rotated clockwise, had ischemia, and had paralysis of its left upper limb. After one hour, the plug was removed from the rat under halothane anesthesia, and the blood flow was thereby reperfused.

In the melatonin administration group, 1 ml of a physiological saline solution containing 6 mg/kg of melatonin was injected using a probe into the stomach of each rat each day for 10 days starting 24 hours after the reperfusion. In the control group, 1 ml of a physiological saline solution was similarly injected into each rat.

After 19 days, the presence of adduction/pronation of the left upper limb and the clockwise rotation were determined for each rat.

To assess the clockwise rotation, each rat was placed on a round plate 2 m in diameter for 5 minutes. If the rat had paralysis of the left upper limb, it rotated clockwise.

To assess the adduction/pronation of the left upper limb, each rat was hung via its tail, and the movement of the left upper limb was observed. If the rat could not voluntarily move the left upper limb, and had paralysis of the left upper limb, the left upper limb was considered to show adduction/pronation.

The results are shown in Table 1.

TABLE 1

|  | during ischemia | 19 days after ischemia |
|---|---|---|
| Adduction/pronation | | |
| Control group | 4/4 | 3/4 |
| Melatonin administration group | 4/4 | 1/4 |
| Clockwise rotation | | |
| Control group | 4/4 | 3/4 |
| Melatonin administration group | 4/4 | 1/4 |

It is clear from the results in Table 1 that the melatonin administration group showed significantly less adduction/pronation of the left upper hand and less clockwise rotation as compared with the control group 19 days after ischemia.

EXAMPLE 2.

In an experiment similar to that as described in Example 1, the adduction/pronation of the left upper limb and the clockwise rotation were determined 11 days after the ischemic incidence.

The results are shown in Table 2.

TABLE 2

|  | during ischemia | 11 days after ischemia |
|---|---|---|
| Adduction/pronation | | |
| Control group | 7/7 | 5/7 |
| Melatonin administration group | 7/7 | 3/7 |
| Clockwise rotation | | |
| Control group | 7/7 | 2/7 |
| Melatonin administration group | 7/7 | 0/7 |

EXAMPLE 3.

Using the rats from the experiment of Example 2, the area of the cerebral infarcted lesion in each rat after 11 days was determined.

The area of the cerebral infarcted lesion was determined by preparing a consecutive section of 50 μm from a cerebral infarcted region of about 3 mm and subjecting the section showing a maximum lesion to the NIH measurement program to determine the area of the maximum lesion.

The results with respect to the area of the infarcted lesion are shown in Table Table 3.

TABLE 3

|  | striatum | cerebral cortex |
|---|---|---|
| control group | 10.62 mm$^2$ | 14.53 mm$^2$ |
| melatonin administration group | 7.15 mm$^2$ | 5.47 mm$^2$ |

It is clear from the results in Table 3 that the melatonin administration group showed less brain damage in both the striatum and the cerebral cortex as compared with the control group. The area of the cerebral infarcted lesion, especially in the cerebral cortex was smaller.

EFFECT OF THE INVENTION

As seen in Tables 1 and 2, the number of rats cured of paralysis of the left upper limb (caused by cerebral infarction through cerebral ischemia) by the treatment with the pharmaceutical composition of the present invention was significantly greater than the number of rats spontaneously cured without the treatment. In W097/20555, the percentage of rats spontaneously cured of the mild motor dysfunction of a foot fault rate of 0.01 was 50%. This percentage is greater than the percentage of rats (30%) cured by the treatment with the "rescue" solution of W097/20555.

Thus, mild motor disturbances as disclosed in W097/20555 could be rather effectively treated by physicotherapies including a motorpathy. It is believed that melatonin gives a minor contribution to the treatment of mild motor disturbances. On the other hand, administration of melatonin is very effective in the treatment of paralysis of the extremities caused by cerebral infarction, as compared with any other available method. Thus, melatonin gives a major contribution to the treatment of paralysis of the extremities caused by cerebral infarction.

Accordingly, the method for the treatment of paralysis of the extremities of the present invention has very strong advantages as compared with known methods for the treatment of mild motor disturbances caused by cerebral ischemia.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. A method for treating a subject suffering from paralysis of the extremities caused by cerebral infraction, comprising administering a therapeutically effective amount of melatonin.

2. The method of claim 1, wherein said melatonin is administered permucosally, orally, enterally, percutaneously, intravenously, by aspiration, by suppository, or by instillation.

3. The method of claim 1, wherein said melatonin is administered orally.

4. The method of claim 1, wherein said melatonin is encapsulated in an encapsulating matrix or a liposome.

5. The method of claim 1, wherein said subject is a human.

6. The method of claim 1, wherein said melatonin is administered in an amount such that the melatonin blood concentration of said subject is 10 ng/ml to 300 μg/ml per day.

7. The method of claim 1, wherein said melatonin is administered in an amount such that the melatonin blood concentration of said subject is 50 ng/ml to 100 μg/ml per day.

8. The method of claim 1, wherein said melatonin is administered orally and in the form of a sustained release composition.

* * * * *